United States Patent [19]
Regan et al.

[11] Patent Number: 5,976,152
[45] Date of Patent: Nov. 2, 1999

[54] METHOD AND SYSTEM FOR DEPLOYING SHAPE MEMORY PROSTHESES WITH HEATED FLUID

[75] Inventors: Barrie F. Regan, Hillsborough; Brent F. Regan, Davis, both of Calif.

[73] Assignee: Regan Stent, Inc., Davis, Calif.

[21] Appl. No.: 08/787,003

[22] Filed: Jan. 28, 1997

[51] Int. Cl.$^6$ ...................................................... A61F 11/00
[52] U.S. Cl. ................... 606/108; 623/1; 606/191
[58] Field of Search ..................... 623/1, 11, 12; 606/108, 151, 190–200; 604/8, 9

[56] References Cited

U.S. PATENT DOCUMENTS

| | | |
|---|---|---|
| 3,868,956 | 3/1975 | Alfidi et al. . |
| 4,503,569 | 3/1985 | Dotter . |
| 4,754,752 | 7/1988 | Ginsburg et al. . |
| 4,795,458 | 1/1989 | Regan . |
| 5,019,075 | 5/1991 | Spears et al. . |
| 5,037,427 | 8/1991 | Harada et al. . |
| 5,354,309 | 10/1994 | Schnepp-Pesch et al. ............. 606/198 |
| 5,466,242 | 11/1995 | Mori ........................................ 606/198 |

FOREIGN PATENT DOCUMENTS

| | | |
|---|---|---|
| 0 626 153 | 11/1994 | European Pat. Off. . |
| WO 94/22379 | 10/1994 | WIPO . |

*Primary Examiner*—Glenn K. Dawson
*Attorney, Agent, or Firm*—Townsend and Townsend and Crew LLP

[57] ABSTRACT

A system for delivering shape memory alloy prosthesis includes a catheter, a fluid injector and a controller. The catheter includes a fluid lumen coupled to the fluid injector and one or more openings at its distal end which are at least partially disposed beneath the prosthesis. The catheter further includes a thermocouple at its distal end for monitoring the temperature of the prosthesis in situ to minimize thermal damage to fluids and tissue within the body lumen. A fluid is heated to an initial temperature, and then delivered through the openings to the prosthesis, and thermal energy is directly transferred to the prosthesis to expand the prosthesis at a temperature above the body temperature. The temperature and flow rate of the fluid is precisely controlled such that the prosthesis is expanded, and thermal damage to the body lumen is minimized.

20 Claims, 5 Drawing Sheets

METHOD AND SYSTEM FOR DEPLOYING SHAPE MEMORY PROSTHESES WITH HEATED FLUID

This patent application references Disclosure Document 367,354, filed on Dec. 20, 1994, in the U.S. Patent Office. It is requested that the contents of the disclosure be incorporated into the prosecution file established for the present application. This application is also related to concurrently filed and commonly assigned patent application entitled "Method and System For Deploying Shape Memory Prostheses", naming Barrie F. Regan and Brent F. Regan as co-inventors, the complete disclosure of which is incorporated herein by reference.

BACKGROUND OF THE INVENTION

1. Field of the Invention

The present invention relates generally to medical methods and devices. More particularly, the present invention relates to methods and apparatus for delivering and expanding prostheses composed of shape memory alloys within blood vessels and other body lumens.

In percutaneous transluminal coronary angioplasty (PTCA) procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and, upon withdrawal, restores adequate blood flow through the diseased region.

While angioplasty has gained wide acceptance, it continues to be limited by two major problems, abrupt closure and restenosis. Abrupt closure refers to the acute occlusion of a vessel immediately after or within the initial hours following the dilatation procedure. This complication occurs in approximately one of twenty cases and frequently results in myocardial infarction and death if blood flow is not quickly restored. Restenosis refers to the re-narrowing of an artery after an initially successful angioplasty. Occurring usually within the initial six months after angioplasty, and restenosis afflicts approximately one in three cases. That is, approximately one in three patients will require additional revascularization procedures.

Many different strategies have been tried with different degrees of success to reduce restenosis and abrupt closure, including pharmacologic (e.g., systemic and localized administration of anti-proliferative agents and other drugs) and mechanical (e.g., prolonged balloon inflations, atherectomy, laser angioplasty, post-angioplasty thermal conditioning, and stenting).

Of particular interest to the present invention, the intravascular delivery and implantation of stents to a blood vessel following balloon angioplasty procedures has proven to be of great value. The first stent to achieve widespread acceptance is the Palmaz-Schatz stent available from Johnson & Johnson Interventional Systems, a division of Ethicon, Inc., Somerville, N.J. The Palmaz-Schatz stent is a slotted tube formed from a malleable material. For delivery to the target site, the stent is usually placed over the balloon of a balloon delivery catheter having a non-distensible balloon. The angioplasty balloon catheter is then exchanged with the delivery catheter, and the stent positioned at the angioplasty treatment site. The balloon of the delivery catheter is then inflated to expand the stent in situ in order to implant the stent within the blood vessel.

A second class of stents is commonly referred to as "self-expanding stents" or "resilient stents" (in contrast to malleable stents as discussed above). This class of stent is defined primarily by the materials from which the stent is fabricated as well as the method in which the stent is retained and deployed. The materials of self-expanding stents may be resilient (spring-like) so that the stent may be delivered in a radially constrained state and implanted by releasing the stent from the constraint, whereby the stent springs back to its larger diameter configuration.

Of specific interest to the present invention, the stents may be formed from shape memory alloys where the stents are delivered in a reduced diameter configuration and subjected to conditions which cause a phase change in the material of the stent which in turn causes radial expansion of the stent structure within the blood vessel. Most commonly, such stents are formed from a nickel titanium alloy and are delivered in a deformed, smaller diameter configuration. Such stents are heated in situ to recover their original "memorized" larger diameter configuration. Typically, such alloys exhibit a crystallographic transformation from a martenistic structure at a lower temperature prior to delivery to an austenitic structure at a higher temperature to which they are subsequently exposed. In some cases, the stents are quickly heated to a temperature somewhat above body temperature when ready for deployment in the blood vessel lumen. In other cases, transformation to the austenitic phase will occur when the stent is exposed to body temperature.

At present, the use of shape memory stents which undergo a phase change and expand at a temperature between room temperature and body temperature is most common. Such stents may be stored at room temperature (although precautions should be taken to make sure that the phase change temperature is not exceeded) and will expand automatically when introduced to a blood vessel or other body lumen. In this way, there is no need to perform a separate deployment step, e.g. delivery of heated saline. Such methods are disadvantageous, however, in several respects. First, because of the relatively small temperature difference between room temperature and body temperature, it can be difficult to control the transition temperature of the stent material with sufficient accuracy. Moreover, the transition temperature being so close to room temperature requires that precautions be taken so that the transition temperature is not accidentally exceeded prior to deployment. Additionally, the stent will usually begin expanding while still contained within a delivery catheter or sheath, thus making final deployment and positioning of the stent problematic.

While the deficiencies just discussed are overcome by use of a stent which is deployed by heating to a temperature above body temperature, such stents and delivery systems suffer from a number of drawbacks of their own. For example, the delivery of a heated fluid through a catheter can be difficult to control, and it can be difficult to assure that the deployment temperature is reached. Use of saline above about 60° C. and/or excessive volumes of heated saline can also cause vessel spasms and/or fibrillation of the heart. In fact, the extent of tissue damage typically increases almost exponentially as the temperature increases above 60 C. While it has been proposed to employ radio frequency energy to inductively heat shape memory stents to cause a phase change in transition, such energy can be deleterious to tissue and expose the patient to other forms of risk.

For these reasons, it would be desirable to provide improved methods and systems for delivering shape memory stents and prostheses to body lumens, such as blood vessels. In particular, it would be desirable to provide methods and systems for the in situ heating of stents, where the heating can be carefully controlled to open the shape memory stent in a desirable fashion. The methods and systems should provide for rapid and complete opening of the shape memory stents without subjecting the patient to undue risks associated with heat transfer. The heating methods should avoid collateral damage to the tissues and membranes surrounding the prosthesis to be expanded, and in particular should avoid inductive radio frequency exposure. The present invention is intended to address at least some of these concerns.

2. Description of the Background Art

Vascular stents and prosthesis composed from shape memory alloys, such as nitinol, are described in a number of patents and published applications including U.S. Pat. Nos. 3,868,956; 4,503,569; 4,795,458; 5,037,427; WO 94/22379; and EP 626 153. The use of heated saline for effecting a phase change and expanding a shape memory stent is disclosed in U.S. Pat. Nos. 4,795,458 and 5,037,427. The use of radio frequency induction for effecting a phase change and expanding a shape memory stent is disclosed in EP 626 153. Heated balloon catheters for performing thermally assisted angioplasty are described in U.S. Pat. Nos. 4,754,752 and 5,019,075.

SUMMARY OF THE INVENTION

According to the present invention, methods, systems, and apparatus are provided for the delivery of shape memory alloy stents to target locations within body lumens. While particularly intended for post-angioplasty delivery of intravascular stents, the method would also find use with the delivery of other stents, grafts, and the like, to other body lumens, such as the delivery of urethral stents for the treatment of prostate conditions, the delivery of esophageal stents, the delivery of bile duct stents, fallopian tube stents, parenchymal stents, and the like. The tubular prosthesis to be delivered will be composed at least in part from a shape memory alloy of the type which expands from a narrow diameter configuration (where the alloy is in the malleable, martensic phase) to an expanded configuration (where the alloy is present in the superelastic, austenitic phase), usually being a nickel titanium alloy such as the commercially available alloy known as NITINOL®. The present invention provides for improved methods and systems for the in situ heating and deployment of such stents at target sites within body lumens.

In a first aspect of the present invention, a system for implanting such tubular prostheses comprises a catheter having a proximal end, a distal end, a fluid lumen therebetween and one or more openings near the distal end. The tubular prosthesis is mounted at least partially over the distal openings in the catheter for delivering a heated fluid, e.g., blood, isotonic saline or dye, through the openings to transfer heat directly to the prosthesis, causing phase transition and resultant radial expansion. The system further includes a controller for controlling the flow of the heated fluid to the catheter so as to control a temperature of the tubular prosthesis or a region surrounding the prosthesis. Careful control of the flow of the heated fluid into the catheter decreases the volume of fluid delivered into the body lumen and the time required to heat the prosthesis. This reduces overheating of the blood vessel, which minimizes vessel spasms and/or fibrillation of the heart.

The system will usually include a heat source connected to the controller to heat the fluid and a fluid injector coupled to the controller for injecting the fluid into the fluid lumen of the catheter after the fluid has been heated to an initial, preselected temperature. The initial temperature is selected such that the fluid is hot enough to transfer heat directly to the prosthesis, causing phase transition and resultant radial expansion, but cool enough to minimize damage to the lumenal wall from overheating. With a standard length delivery catheter, the initial temperature will typically be about 70 to 80 degrees Celsius and preferably about 75 degrees Celsius. At this temperature, the fluid will generally cool to a temperature of about 50 to 59° C., preferably about 55 to 59° C., by the time it reaches the distal end of the catheter and enters the body lumen. This temperature is usually sufficient to heat the prosthesis to its phase transition temperature without causing significant tissue damage.

In an exemplary configuration, the controller will ensure that the fluid injector delivers fluid at a controlled rate through the catheter to the tubular prosthesis. Preferably, the fluid will be delivered relatively quickly, e.g., at a rate of about 1–3 cc/second, preferably at least 2 cc/second, so that the heat transfer process proceeds relatively quickly. Heating the prosthesis quickly with a relatively high flow rate decreases the amount of energy that is applied, which may reduce thermal damage to tissue and/or fluids within the body lumen.

In an exemplary embodiment, one or more temperature-sensing element(s) are positioned near the openings at the distal end of the catheter. The temperature-sensing element (s) are connected to the temperature controller and the fluid injector in order to monitor the temperature of the prosthesis in situ, and to minimize thermal damage to the body lumen. Preferably, the temperature controller modulates or discontinues fluid flow from the fluid source based on the temperature at the thermocouple to control the temperature of the tubular prosthesis or a region surrounding the prosthesis. Preferably, the fluid injector will completely discontinue the injection of fluid into the catheter when the temperature sensing element(s) reach a set point temperature, usually about 50 to 59° C. and preferably about 55–59° C.

One of the advantages of the present invention is that it is usually not necessary to block fluid flow within the body lumen in order to transfer heat to the prosthesis. The heated fluid generally displaces blood and other fluids surrounding the prosthesis for a long enough time to heat the prosthesis and cause a resultant phase change. To facilitate this process, however, the catheter may include an inflatable balloon located adjacent to and upstream of the prosthesis. In such cases, the balloon can be fully or partially expanded in order to reduce or temporarily block blood flow to the prosthesis in order to enhance heat transfer between the thermally conductive fluid and the prosthesis. Since the expansion of the stent can be achieved very rapidly, on the order of several seconds, such partial or complete blockage of blood flow need only occur for a very short period of time.

In a second aspect of the present invention, a method for implanting a tubular prosthesis within a body lumen comprises providing a tubular prosthesis, generally as described above, and providing a deliver catheter, also generally as described above. The delivery catheter is used to intraluminally position the prosthesis at the target site within the body lumen. The heated fluid is then delivered through an internal lumen of the catheter to its distal end for a time and at a temperature sufficient to expand the tubular prosthesis from its narrow diameter to its expanded diameter configuration. The heated fluid directly contacts the prosthesis and, therefore, directly transfers heat thereto. The body lumen will usually be a blood vessel, but could also be the urethra, the ureter, the bile duct, or the esophagus. Most commonly, the body lumen is an artery and the target site is an occlusion within the artery, such as a coronary artery occlusion.

Specifically, the thermally conductive fluid is heated to a initial temperature (e.g., about 75 degrees Celsius), and then delivered at a controlled rate through the fluid lumen of the catheter to the openings at its distal end. The fluid directly transfers heat to the prosthesis, causing a phase change and expansion of the prosthesis to a larger diameter within the body lumen. The temperature sensing element ensures that the temperature at the distal end of the catheter remains below a set point temperature of about 50 to 59° C., preferably about 55 to 59° C. In addition, a controlled volume of the heated fluid is delivered to the body lumen to minimize vessel spasms, defibrillation of the heart and other adverse consequences that may result from large volumes of heated fluids within the vasculature.

DESCRIPTION OF THE SPECIFIC EMBODIMENTS

Figure 1:
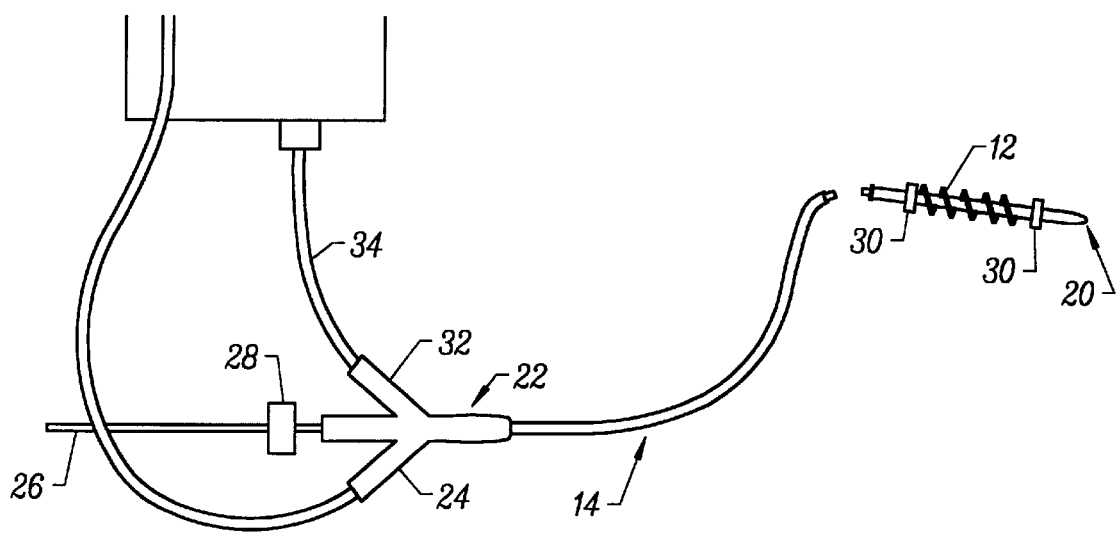
FIG. 1 is a perspective view of a system including a tubular prosthesis, a delivery catheter, a controller, and a fluid injection, in accordance with the principles of the present invention.

The present invention provides methods, systems, and devices for the intraluminal delivery and implantation of tubular prostheses composed at least in part from a shape memory alloy. By "intraluminal," it is meant that the delivery occurs at a target site within a body lumen, usually being within the patient vasculature, more usually being within the arterial system, including the coronary arteries, the peripheral arteries, and the cerebral arteries. The methods and devices of the present invention, however, are not limited to use in the vascular system, and may also be advantageously employed in other body structures, including the prostate via the prostatic urethra, (e.g., to treat benign prostatic hypertrophy (BPH), or adenocarcinoma), the fallopian tube via its lumen (to treat strictures), brain parenchyma (to treat Parkinson's disease), the bile duct, the esophagus, and the like.

The "target site" within the body lumen will usually be diseased or be suspected of being diseased. In the case of vascular treatment, the target locations will usually be occluded or stenotic regions which have previously been treated by conventional balloon angioplasty procedures using a balloon angioplasty catheter or other primary treatment procedures, such as atherectomy, laser angioplasty, ultrasonic ablation, or the like. Such regions are referred to hereinafter as "occlusions."

The apparatus and methods of the present invention are intended for the delivery of tubular prostheses to the target site in the body lumen. Such prostheses include both stents and graft structures, particularly intravascular stents and grafts of the type used to maintain vessel patency following balloon angioplasty and other primary treatment procedures. The tubular prostheses will be composed at least in part from a shape memory alloy which displays a phase transition from its martensic (malleable) phase to its austenitic (superelastic) phase at a temperature above body temperature (37° C.), typically at a temperature in the range from 37° C. to 70° C., more preferably from 50° C. to 59° C. It will be appreciated that the precise transition temperature will depend on the particular composition of the shape memory alloy, the time and temperature parameters of the alloy heat treatment, hot and cold forming processes, and the like. The particular transition temperature will usually be accurate within a fairly narrow range, typically ±3° C. Preferred is the use of a family of nickel-titanium alloys, such as NITINOL® alloys, which are available with a wide variety of specific transition temperatures. These materials may be obtained as wires, ribbons, tubes, and the like, each of which may be fabricated into particular expansible prostheses structures as described in more detail below.

The tubular prostheses will usually be formed entirely from the shape memory alloy, but could be formed with only a portion being formed from the alloy. In particular, tubular graft structures will often comprise a fabric membrane which is attached to a metallic frame. In such cases, the membrane would of course not be composed of the shape memory alloy while all or a portion of the metallic frame would be. In particular, it would be possible to form a portion of the metallic frame of the tubular prostheses from other than the shape memory alloy, e.g. in prostheses formed from counterwound helices, one helix could be formed from the shape memory alloy while the other was formed from another material. The present invention is not limited to the particular construction of the tubular prosthesis, but rather will apply to any tubular prosthesis which can be expanded by exposure to a temperature above body temperature for an appropriate time, as discussed in more detail below.

The tubular prosthesis of the present invention may have a wide variety of specific geometries, including virtually any conventional stent or graft geometry. Exemplary geometries include helical ribbons, helical wires, serpentine structures, zig-zag stents, slotted tubes, and the like. Specific helical ribbon designs are disclosed in U.S. Pat. Nos. 4,795,458 and 5,037,427, the disclosures of which are incorporated herein by reference. Another specific design for a zig-zag type stent composed of a shape memory alloy is provided in PCT published application WO 94/17754, the full disclosure of which is incorporated herein by reference. Another specific design is described in connection with FIG. 6 below.

The tubular prostheses will be fabricated so that they possess an expanded diameter in the austenitic phase. That is, the tubular prosthesis will be formed and heat-treated so that it "memorizes" the desired final diameter and returns to such diameter when heated to a temperature above the transition temperature so that it reenters to the austenitic phase. The prosthesis will be reduced to its narrow diameter configuration by cooling below the transition temperature so that the shape memory alloy enters its martensic (malleable) phase. In the malleable phase it can be constricted to the desired delivery diameter. Often, it will be constricted directly over the delivery catheter and be maintained in the constricted configuration until it is delivered to the target site within the body lumen and is exposed to a temperature above the transition temperature (which is above body temperature). Specific fabrication methods for shape memory alloy stents are well known and described in the patent and technical literature.

Catheters according to the present invention will comprise a catheter body having a proximal end and a distal end, and dimensions suitable for delivery to the intended intraluminal target site. For intravascular uses, the catheter body will typically have a length in the range from about 50 cm to 250 cm, usually from about 100 cm to 175 cm. The catheter body will have an outside diameter in the range from 1 French (1 Fr=0.33 mm) to 12 French, typically from 2 Fr to 11 Fr, more usually from 3 Fr to 10 Fr. The catheter body will usually include at least a single lumen for introduction over a conventional guidewire, and may also include other lumens for other purposes, such as delivery of a heat transfer fluid to a balloon as described hereinafter. The guidewire lumen may extend for the full length of the catheter body, for over-the-wire deployment, or may extend only partly through the distal end of the catheter body, for rapid exchange deployment. The catheter body will be formed from conventional materials, typically by extrusion of polymeric materials, such as polyethylenes, including polyethyleneterephthalate, polyimides, polyesters, polyurethanes, polyvinylchlorides, and the like.

The catheter will include a fluid lumen extending from a proximal hub to its distal end, and one or more holes at the distal end for delivering heated fluid to the prosthesis. Usually, the catheter will have a plurality of such holes, e.g., 2–4 holes, spaced around its circumference so as to deliver the fluid substantially uniformly to the prosthesis. This helps to ensure that the prosthesis is heated uniformly, so that the entire prosthesis will undergo a phase change and resulting expansion within the body lumen. The number of holes and their diameter will preferably be selected to minimize the reduction of the fluid flow rate as it passes from the catheter lumen through the holes (discussed below).

The system of the present invention will include one or more controllers for controlling the injection rate of the heated fluid, the temperature of the heated fluid prior to injection and the temperature at the distal end of the catheter within the body lumen. The controller will usually include a fluid injector, such as a syringe, coupled to a heat source, such as a resistive heating element, for heating the fluid within the syringe. The controller will also include one or more temperature sensing elements, such as a thermocouple, coupled to the fluid injector for monitoring the temperature of the fluid therein. Preferably, the controller will include a temperature controller coupled to a drive, such as an electric or pneumatic motor. The temperature controller monitors the temperature of the fluid and actuates the drive (either automatically, or manually) when the fluid has reached a initial temperature. The initial temperature will be selected such that, when the fluid reaches the distal end of the catheter, it is at a temperature sufficient to heat the prosthesis to its phase change temperature, but low enough to minimize overheating of tissue and fluids within the body lumen (e.g., typically about 55 to 59 degrees Celsius). For a conventional delivery catheter, the initial temperature will be in the range of about 70 to 80 degrees Celsius and preferably about 75 degrees Celsius.

The system will also usually include a second temperature controller coupled to one or more thermocouples or similar temperature sensing elements at the distal end of the catheter. The second temperature controller functions to monitor the temperature at the distal end of the catheter, and to discontinue injection of fluid when the sensing element reaches a set point temperature. The set point temperature will usually be in the range of about 55 to 59 degrees Celsius for the reasons discussed above. Alternatively, the second temperature controller may modulate or throttle the fluid flow as the thermocouple reaches the set point temperature. Of course, it will be appreciated that the system may include only one temperature controller that performs both of the functions described above.

The catheter may optionally include one more inflatable balloon(s) for any one of several purposes. In some instances, the catheter may include a non-distensible balloon intended for performing a balloon angioplasty prior to implantation of the tubular prosthesis. Such angioplasty balloons will usually, but not necessarily, be provided immediately distal to the tubular prosthesis on the catheter. In that way, the balloon may be positioned within the target occlusion, inflated to treat the occlusion, and the catheter thereafter advanced to properly position the prosthesis within the treated occlusion. It is of course not necessary for the catheter to include an angioplasty balloon (or any other primary treatment modality), and the catheter can be used after any primary treatment is performed with a separate catheter.

One of the advantages of the present invention is that it is usually not necessary to block fluid flow within the body lumen in order to transfer heat to the prosthesis. The heated fluid generally displaces blood and other fluids surrounding the prosthesis for a long enough time to heat the prosthesis and cause a resultant phase change. To facilitate this process, however, the catheters of the present invention may be provided with a balloon employed to slow or block blood flow in order to enhance heat transfer between the heated fluid and the prosthesis. The balloon, which may be distensible (elastomeric) or non-distensible, could be provided either distal to or proximal to the prosthesis. The balloons may then be inflated to partially or totally occlude the blood vessel, thus limiting the heat loss resulting from blood flow. After the prosthesis is expanded, the balloon may be deflated to re-establish blood flow. As the prosthesis will be expanded for a very short period of time, typically on the order of seconds as discussed below, the interruption of blood flow will not be a significant concern.

Referring now to FIG. 1, an exemplary system 10 for delivering a helical prosthesis 12 according to the method of the present invention comprises a delivery catheter 14, a controller 16 and a fluid injector 19 mounted to controller 16. The prosthesis 12 is carried between a pair of radiopaque markers 30 on the catheter 14 which are used to assist in implantation. Radiopaque markers 30 may include a variety of radiopaque materials, such as platinum, gold, tantalum and the like.

The system will also include a heat source, such as a resistive heating element coupled to a power supply, (not shown) for heating the fluid within fluid injector 19. Generally, the fluid injector 19 will contain a sufficient volume of fluid to heat and expand the prosthesis 12. However, it will be recognized that an additional source of fluid may be coupled to the fluid injector 19. As shown, delivery catheter 14 has a distal end 20, a hub 22 at its proximal end, an axial lumen 23 (FIG. 4) for delivering fluid to distal end 20, and a second internal lumen 25 (FIG. 4) for receiving an electrical wire 34 coupled to a thermocouple 50 (FIG. 3) at distal end 20 of catheter 14. Hub 22 generally includes a fluid connector 24 coupled to axial lumen 23 for receiving heating medium from fluid injector 19, a guide wire port 28 for receiving a conventional or non-conventional guide wire 26 and a third port 32 for receiving thermocouple wire 34.

Figure 2:
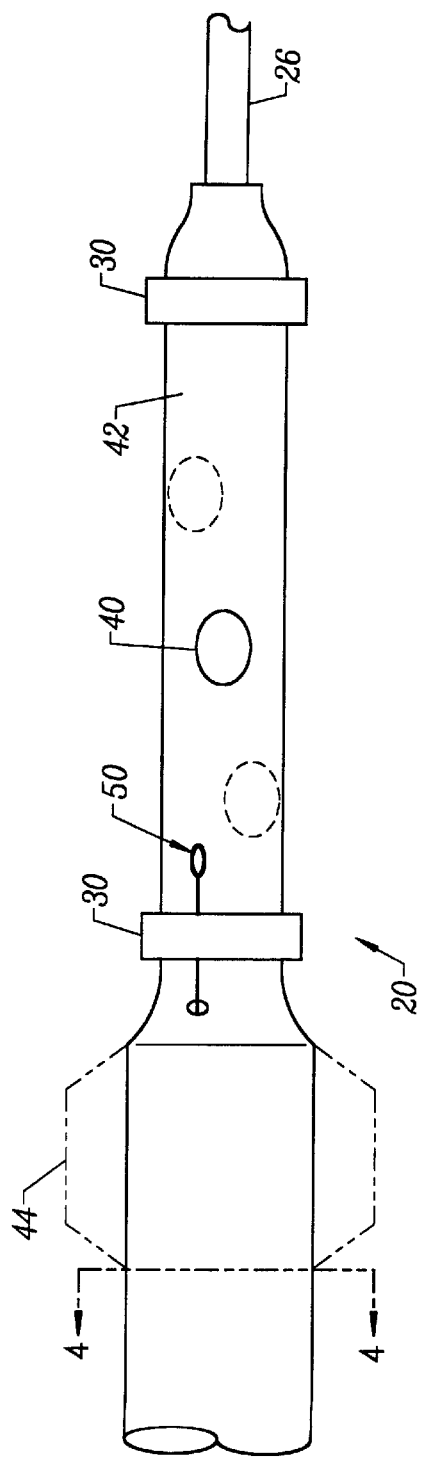
FIG. 2 is a detailed view of the distal end of the catheter of FIG. 1.
Figure 4:
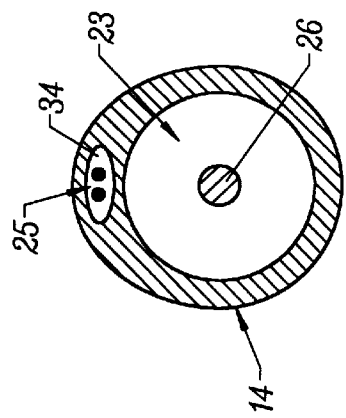
FIG. 4 is a sectional view of the catheter taken along line A—A of FIG. 2.
Figure 3:
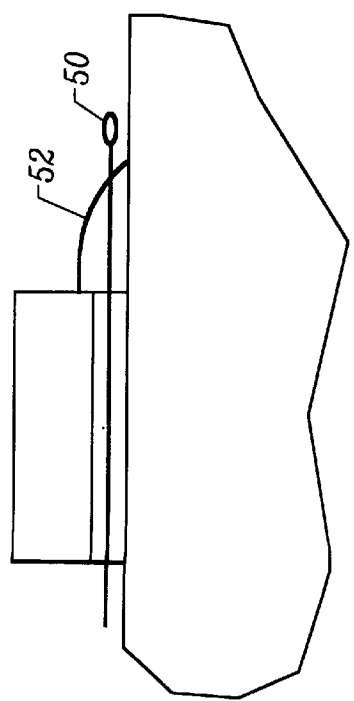
FIG. 3 is an expanded view of a portion of the catheter of FIG. 2, illustrating a thermocouple for detecting the temperature at the distal end of the catheter.

FIGS. 2–4 illustrate distal end 20 of catheter in more detail. The tubular prosthesis 12 (not shown in FIGS. 2–4)

is wrapped around a smaller diameter portion 42 of catheter 14 so that the outer diameter of portion 42 and prosthesis 12 (in its reduced diameter or martensic state) is not larger than the outer diameter of the rest of the catheter. Smaller diameter portion 42 may be formed integrally with the rest of catheter, or it may be formed separately and attached with suitable means, such as adhesive. An inflatable balloon 44 may optionally be provided proximal to the prosthesis 12. The balloon would be connected to an additional inflation port by an internal lumen within catheter 14. The inflation balloon may serve to inhibit blood or other fluids in the body lumen from washing the thermally conductive fluid downstream of prosthesis 12 (at least long enough for the fluid to transfer a sufficient amount of heat to prosthesis 12). A more detailed description of this concept can be found in concurrently filed and commonly assigned patent application entitled "Method and System For Deploying Shape Memory Prostheses", the complete disclosure of which has previously been incorporated herein by reference.

As shown in FIG. 2, catheter 14 includes a plurality of lateral holes 40 on smaller diameter portion 42. Lateral holes 40 are fluidly coupled via lumen 23 and injection port 24 to fluid injector 19. A temperature sensing element 50, such as a thermocouple or thermistor, is provided on the distal end 20 of catheter 14. As shown in FIGS. 2 and 3, the thermocouple 50 will be positioned underneath prosthesis 12 between radiopaque markers 30. Thermocouple 50 is preferably attached to catheter 14 with a suitable adhesive 52 to ensure that the thermocouple 50 remains in place during implantation of the prosthesis 12. The temperature sensing element 50 will be able to monitor temperature in the region of the prosthesis 12, and it will be appreciated that two or more sensing elements may be provided if it is desired to obtain an average temperature or temperature profile.

Figure 5:
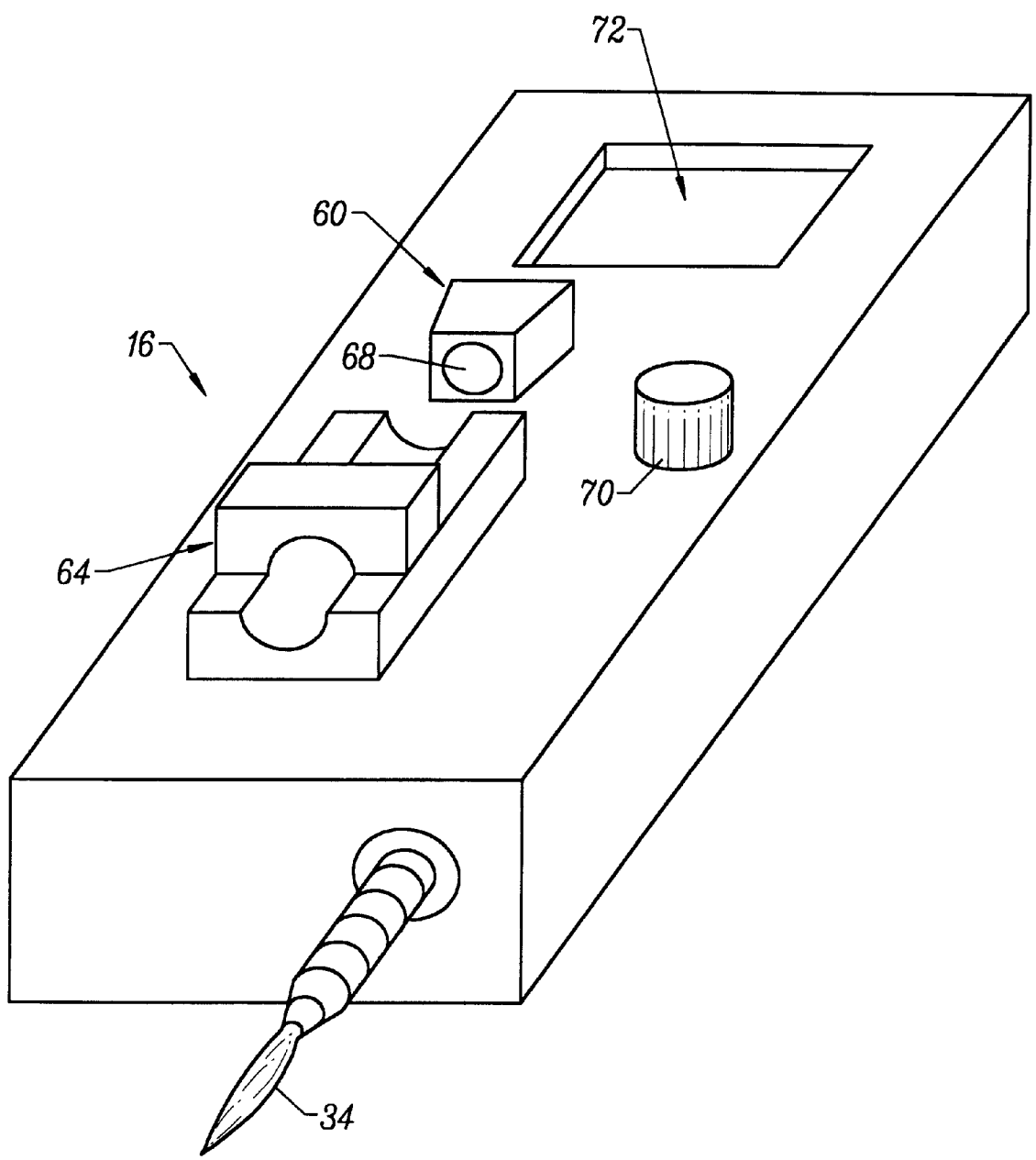
FIG. 5 is a detailed view of the controller of the system of FIG. 1.

Referring to FIG. 5, controller 16 includes two temperature controllers (not shown), a drive 60 for actuating fluid injector 19 and controlling the fluid flow rate into catheter 14, and a heat source (not shown) for heating the fluid injector 19 to a initial temperature prior to injection of the fluid. Preferably, injector 19 (FIG. 1) is a standard syringe coupled to fluid port 24 which is, in turn, coupled to the fluid lumen 23 within catheter 14. Syringe 19 is attached to a mount 64 on controller 16 such that the syringe plunger 66 is facing drive 60 (see FIG. 1). In the exemplary embodiment, drive 60 includes a geared electric motor (not shown) electrically coupled to one of the temperature controllers. The electric motor drives a lead screw (not shown) that, in turn, drives a threaded nut 68 that pushes plunger 66 of syringe 19 downward to inject fluid into catheter 14. The geared electric motor preferably drives the lead screw at a constant rate so that plunger 66 will inject the fluid at a constant rate into catheter 14, usually about 1 to 3 cc/second, and preferably at least about 2 cc/second. This rapid, controlled fluid flow rate increases the heat transfer process, thereby reducing the time that the body lumen is exposed to the hot fluid.

Referring again to FIG. 5, controller 16 will also include a button 70 or other user-actuatable mechanism for initiating the injection of the fluid from syringe 19 to catheter 14. Controller 16 may also include a second button (not shown) for initiating the heating of syringe 19. A display 72 indicates the temperature of the fluid within syringe 19, as well as the temperature at thermocouple 50 near the distal end 20 of catheter 14. Display 72 may also include an alarm or other means for indicating to the surgical team when the syringe 19 has been heated to the preselected, initial temperature.

Figure 6:
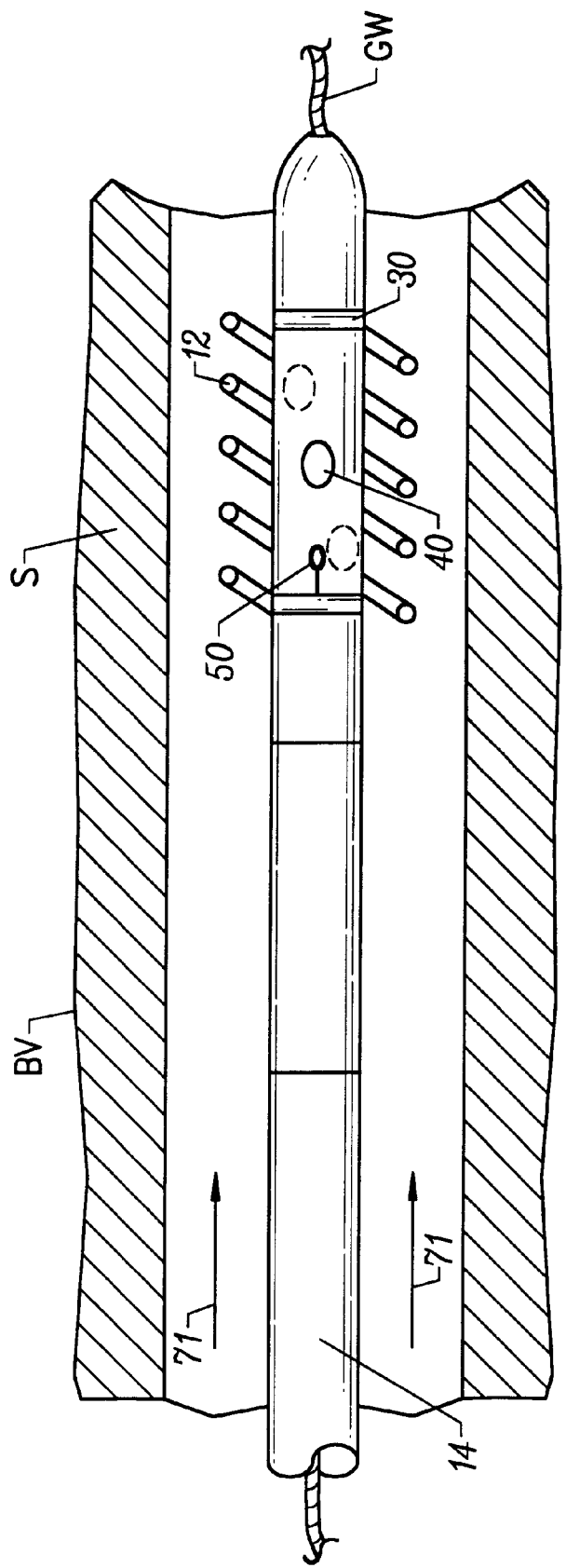
FIG. 6 illustrates use of the delivery system of FIG. 1 for planting a tubular prosthesis within a blood vessel.

Referring now to FIG. 6, use of the catheter 14 for delivering the prosthesis 12 to a target site S in blood vessel BV will be described. After angioplasty or other primary treatment of the treatment site S, the catheter 14 is introduced over guidewire GW so that the prosthesis 12 is within the target site S. A balloon (not shown) may then be partially or fully inflated in order to inhibit blood flow through the blood vessel lumen (blood flow direction is indicated by arrows 71). Positioning of the prosthesis 12 is facilitated by observing the radiopaque markers 30 by conventional fluoroscopic methods.

Before or after blood flow is reduced, the syringe 19 is heated by the heat source. When the syringe 19 has reached the initial temperature, e.g., about 75 degrees Celsius, the controller will indicate to the surgeon that the fluid is ready to be injected (e.g., visually on display 72 and/or aurally with an alarm). The surgeon then initiates the injection of fluid by pressing button 70, which causes an electric current to be applied to the geared electric motor. The motor drives nut 68 into plunger 66 (FIG. 1) at a controlled rate, as discussed above. The fluid is delivered through fluid lumen 23 in catheter 14 and lateral holes 40 to the tubular prosthesis 12. The fluid will cool down on the way through catheter 14 so that the temperature of the fluid at holes 40 is usually about 55 to 59 degrees Celsius. The heated fluid directly contacts prosthesis 12 and, therefore, directly transfers heat to the prosthesis 12. As the prosthesis warms up, it will undergo a phase change and expand against the body lumen, as shown in FIG. 6. Once thermocouple 50 reaches the set point temperature, e.g., about 55 to 59 degrees Celsius, another temperature controller or the same temperature controller ceases the electric current to drive 60 such that syringe 66 discontinues injection of the fluid into catheter 14. This temperature control of fluid prevents the temperature within the body lumen from getting too high, which minimizes damage to the lumenal walls and the blood therein. After complete expansion, the balloon is deflated and the catheter is removed from the patient.

Figure 7A:
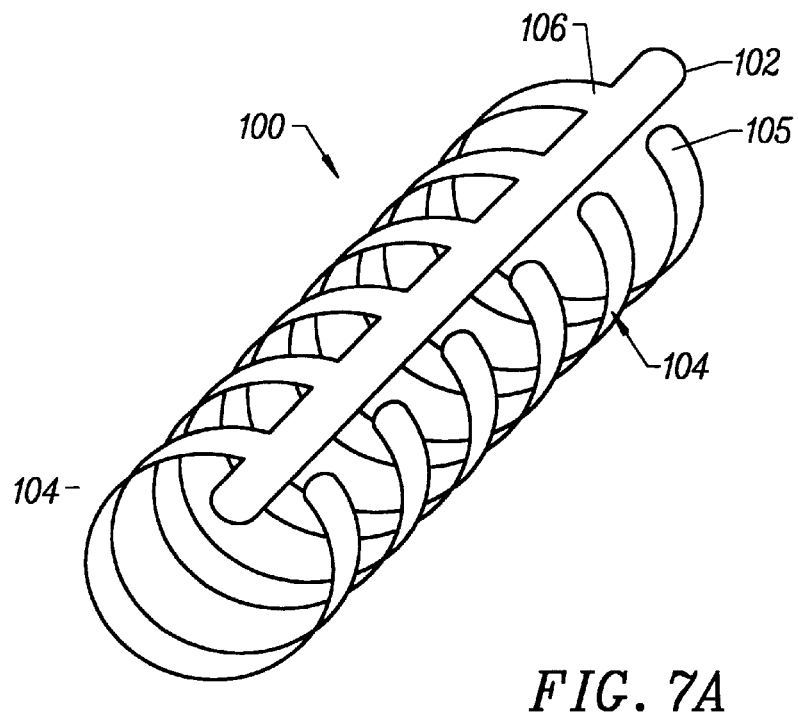
FIGS. 7A and 7B illustrates an alternative stent design which may be delivered by the apparatus and method of the present invention.
Figure 7B:
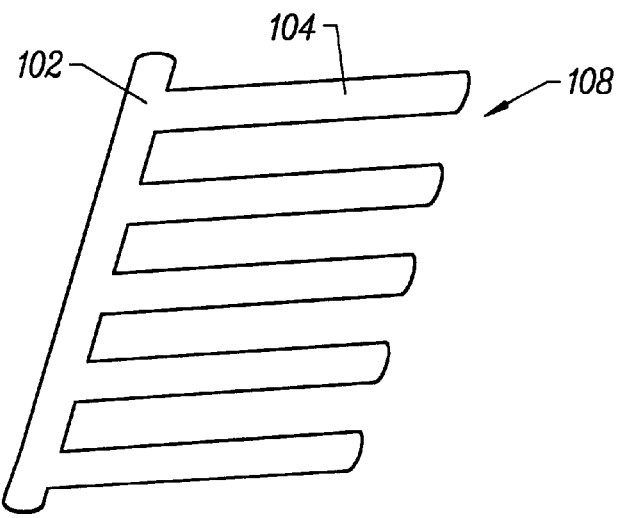

FIGS. 7A and 7B illustrate an alternate stent design which may be conveniently delivered by the catheter and method of the present invention. Instead of being formed as a continuous helix, stent 100 comprises a spine 102 which has a plurality of ribs 104 attached thereto. Ribs 104 each have a first end 106 extending from one side of the spine 102 and a second end 105 almost, but not quite, contacting the other side of the spine 102. The stent 100 is shown in its as manufactured (smaller diameter or martensic) configuration in FIG. 7A, and it will be appreciated that the stent can be radially collapsed over a delivery catheter according to the method of the present invention and thereafter deployed using heated fluid as described above. In its radially expanded configuration within the body lumen, the ribs 104 may overlap the spine 102. The stents 100 may be formed by welding separate components to the spine 102 to form the ribs. Preferably, however, the spine 102 and ribs 104 will be cut from a single flat sheet to form a comb-shaped blank 108 (see FIG. 7B) which is thereafter shaped and heat treated to form the coiled stent. The stent could also be formed with alternating ribs extending from either side of the spine so that the ribs are interdigitated with each other, or any other geometry for that matter. The materials and dimensions of the stent 100 will be generally as set forth above for the helical stents.

Although the foregoing invention has been described in some detail by way of illustration and example, for purposes of clarity of understanding, it will be obvious that certain changes and modifications may be practiced within the scope of the appended claims.

What is claimed is:

1. A system for implanting a tubular prosthesis within a body lumen, said system comprising:

a catheter having a proximal end, a distal end, a fluid lumen therebetween and an opening near or at the distal end coupled to the fluid lumen for directing a heated fluid;

a temperature sensing element near the opening on the catheter for monitoring the temperature of the heated fluid from the lumen in situ;

a tubular prosthesis mounted at least partially over the opening at the distal end of the catheter, said prosthesis being composed at least in part from a shape memory alloy and having a narrow diameter configuration and an expanded diameter configuration;

a heat source; and a controller coupled to the catheter and disposed to control flow of the heated fluid through the fluid lumen of the catheter to the opening at the distal end so as to directly transfer a sufficient amount of heat from the heated fluid to the prosthesis to expand the prosthesis to the expanded diameter configuration without causing substantial thermal damage to tissue or fluids within the body lumen, said controller comprising a temperature controller coupled to the temperature sensing element and the heat source.

2. A system as in claim 1, further comprising a fluid injector coupled to the temperature controller for injecting the fluid into the fluid lumen of the catheter, the controller actuating the fluid injector after the fluid has been heated to a preselected temperature.

3. A system as in claim 2, wherein the preselected temperature and a flow rate of the heated fluid is selected such that the heated fluid will be at a temperature of about 55 to 59 degrees Celsius when the fluid reaches the opening at the distal end of the catheter.

4. A system as in claim 2, wherein the preselected temperature is about 70 to 80 degrees Celsius.

5. A system as in claim 2, further comprising a drive coupled to the fluid injector for actuating the fluid injector, the drive being operable to inject the fluid at a controlled flow rate into the catheter.

6. A system as in claim 5, wherein the controlled flow rate is about 2 to 3 cc/second.

7. A system as in claim 2 wherein the controller is operable to discontinue injection of the fluid into the catheter when the temperature sensing element at the distal end of the catheter reaches a set point temperature.

8. A system as in claim 7, wherein the set point temperature is about 55 to 59 degrees Celsius.

9. A system as in claim 1, wherein the tubular prosthesis comprises a spine having a plurality of ribs extending from one side of the spine.

10. A method for implanting a tubular prosthesis within a body lumen, said method comprising:

providing a tubular prosthesis composed at least in part from a shape memory alloy and having a narrow diameter configuration and an expanded diameter configuration;

intraluminally positioning a catheter to locate the prosthesis at a target site within the body lumen;

delivering a heated fluid through an opening at a distal end of the catheter to the prosthesis to directly transfer heat to the prosthesis;

controlling delivery of the heated fluid for a time, and at a flow rate to heat tubular prosthesis to a temperature sufficient to expand the tubular prosthesis from its narrow diameter to its expanded diameter configuration without causing substantial thermal damage to tissue or fluids within the body lumen;

measuring the temperature at the distal end of the catheter; and discontinuing the delivery of the heated fluid after the measured temperature reaches a preselected set point temperature.

11. A method as in claim 10 wherein the body lumen is selected from the group consisting of blood vessels, the urethra, the ureter, the bile duct, and the esophagus.

12. A method as in claim 11, wherein the body lumen is an artery and the target site is an occlusion.

13. A method as in claim 10 further comprising heating the fluid to a preselected temperature before the delivering step.

14. A method as in claim 13 wherein the preselected temperature is a temperature selected such that the fluid will not cause substantial thermal damage to the tissue or fluids within the body lumen when the fluid passes through the opening at the distal end of the catheter.

15. A method as in claim 13, wherein the preselected temperature is about 70 to 80 degrees Celsius.

16. A method as in claim 13 further comprising injecting an fluid into the axial lumen of the catheter after the fluid has been heated to the preselected temperature.

17. A method as in claim 16 wherein the fluid is injected at a controlled flow rate.

18. A method as in claim 17 wherein the controlled flow rate is at least about 1 cc/second.

19. A method as in claim 10, wherein the preselected set point temperature is in the range from 55 to 59 degrees Celsius.

20. An improved method for implanting a tubular prosthesis in a body lumen, said method being of the type wherein the prosthesis is heated to a temperature above body temperature to effect expansion resulting from a phase change in the material of the prosthesis, wherein the improvement comprises monitoring the temperature in the region of the prosthesis in situ, and controlling the delivery of a heated fluid to the prosthesis at a target site within the body lumen for a time, a flow rate and at a temperature sufficient to expand the tubular prosthesis from a narrow diameter to an expanded diameter configuration without causing substantial thermal damage to the body lumen.

* * * * *